United States Patent [19]

Jakobsen et al.

[11] Patent Number: 5,328,917
[45] Date of Patent: Jul. 12, 1994

[54] PIPERIDINE COMPOUNDS FOR TREATING ANOXIA, CEREBRAL ISCHEMIA MIGRAINE OR EPILEPSY

[75] Inventors: Palle Jakobsen, Værløse; Anders Kanstrup, Virum; Jane M. Lundbeck, Glostrup, all of Denmark

[73] Assignee: Novo Nordisk A/S, Bagsvaerd, Denmark

[21] Appl. No.: 65,513

[22] Filed: May 20, 1993

Related U.S. Application Data

[63] Continuation of Ser. No. 728,930, Jul. 12, 1991.

[30] Foreign Application Priority Data

Jul. 18, 1990 [DK] Denmark .......... DK1724/90
Jan. 24, 1991 [DK] Denmark .......... DK0117/91

[51] Int. Cl.$^5$ .......... C07D 211/26; A61K 31/445
[52] U.S. Cl. .......... 514/331; 514/317; 514/319; 514/321; 546/196; 546/197; 546/198; 546/205; 546/206; 546/239; 546/234; 546/236
[58] Field of Search .......... 546/196, 197, 229, 234, 546/236, 197, 198, 206, 205; 514/317, 319, 321, 331

[56] References Cited

U.S. PATENT DOCUMENTS

| 3,912,743 | 10/1975 | Christensen | 546/236 |
| 4,571,424 | 2/1986 | Christensen | 546/236 |
| 4,877,799 | 10/1989 | Drejer | 546/197 |
| 5,017,585 | 5/1991 | Jakobsen | 546/197 |
| 5,019,582 | 5/1991 | Drejer | 546/197 |

FOREIGN PATENT DOCUMENTS 0190496 8/1986 European Pat. Off. .
0339579 2/1989 European Pat. Off. .

OTHER PUBLICATIONS

Greenberg "Current Neurology" by Appel, pp. 93-109 (1987).
Scarpelli "Cell Injury" pp. 44-45 Apr., 1986.
Nachshen "The Effect of Some Organic Calcium Antagonist on Cainylux in Presynoptic Nerve Terminals" Mol. Pharm. 16 579-586 (1979).

*Primary Examiner*—C. Warren Ivy
*Assistant Examiner*—Celia Chang
*Attorney, Agent, or Firm*—Steve T. Zelson; Elias J. Lambiris

[57] ABSTRACT

The present invention relates to piperidine derivatives of the formula:

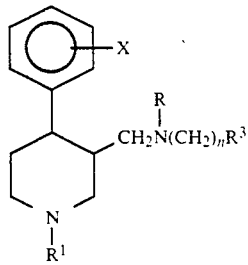

wherein, R, $R^1$, $R^3$, X, and n are defined in the specification, pharmaceutical compositions thereof and methods of treating anoxia, traumatic injury, ischemia, migraine and epilepsy.

10 Claims, No Drawings

PIPERIDINE COMPOUNDS FOR TREATING ANOXIA, CEREBRAL ISCHEMIA MIGRAINE OR EPILEPSY

This application is a continuation application of co-pending application Ser. No. 07/728,930, filed Jul. 12, 1991, the contents of which are incorporated herein by reference.

The present invention relates to therapeutically active piperidine compounds, a method of preparing the same and to pharmaceutical compositions comprising the compounds. The novel compounds are useful in the treatment of anoxia, traumatic injury, ischemia, migraine and epilepsy.

It is well known that accumulation of calcium in the brain cells (calcium overload) is seen after periods of uncontrolled hyperactivity in the brain, such as after convulsions, migraine, anoxia and ischemia. As the concentration of calcium in the cells is of vital importance for the regulation of cell function, an uncontrolled high concentration of the cell calcium will lead to, or indirectly cause the symptoms and possibly also the degenerative changes combined with the above diseases.

Therefore, calcium overload blockers selective for brain cells will be useful in the treatment of anoxia, traumatic injury, ischemia, migraine and epilepsy.

Well known calcium antagonists such as nifedipine, verapamil and diltiazem have activity against peripheral calcium uptake, e.g. in blood vessels and the heart, however, they have shown only very low activity against calcium overload in brain cells.

Accordingly it is an object of the invention to provide novel compounds having activity against calcium overload in brain cells.

The novel compounds of the invention are piperidine compounds having the general formula I

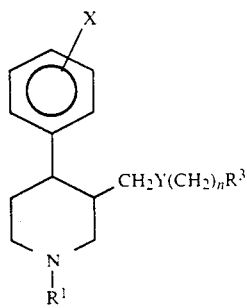

wherein
$R^3$ is 3,4-methylenedioxyphenyl, phenyl, naphthyl, or a 5 or 6 membered heterocyclic group containing one or two N, O or S - atoms being saturated, partly saturated or aromatic which are optionally substituted with one or more halogen, amino, $C_{1-6}$-alkyl mono- or disubstituted amino, $C_{1-6}$-alkoxy, cyano, mono- or poly halogenated $C_{1-6}$-alkyl, $C_{2-6}$-alkenyl, $C_{1-6}$-alkyl, $C_{3-5}$-alkylene, trifluoromethoxy, hydroxy, hydroxy $C_{1-4}$-alkyl, or trifluoromethyl;

n is 0 to 4;

$R^1$ is hydrogen, straight or branched $C_{1-8}$-alkyl, $C_{1-8}$-alkoxy-$C_{1-8}$-alkyl, $C_{3-8}$-cycloalkyl, $C_{2-6}$-alkenyl, $C_{4-8}$-cycloalkylalkyl, acetyl or $C_{2-6}$-alkynyl;

X is one or more amino, $NO_2$, $C_{1-6}$-alkyl mono- or disubstituted amino, $C_{1-8}$-alkanoylamino, carboxy, $C_{1-6}$-alkyl mono- or disubstituted ureido, $C_{1-6}$-alkyl substituted with amino which are optionally mono- or disubstituted with $C_{1-6}$-alkyl, unsubstituted carbamoyl or $C_{1-6}$-alkyl optionally substituted with phenyl and/or hydroxy N-mono or disubstituted carbamoyl, unsubstituted sulfamoyl, $C_{1-6}$-alkyl N-substituted sulfamoyl, $C_{1-6}$-alkyl S-substituted sulfamoyl, $C_{1-6}$-alkyl N- and S-substituted sulfamoyl, or a 5 or 6 membered heterocyclic group containing one or two N, O or S - atoms being saturated, partly saturated or aromatic, the heterocyclic group can be fused to the ring and, when Y is NR and/or n is 1 to 4 X is halogen, $C_{1-6}$-alkyl, $C_{2-6}$-alkenyl, $C_{3-8}$-cycloalkyl, $C_{4-8}$-cycloalkylalkyl, $C_{1-6}$-alkoxy, cyano, mono- or poly halogenated $C_{1-6}$-alkyl, hydroxy or hydrogen;

Y is O, S or NR wherein R is hydrogen or $C_{1-5}$-alkyl, or a salt thereof with a pharmaceutically-acceptable acid.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts.

The invention also relates to a method of preparing the above mentioned compounds. These methods comprise a) reacting a compound having the formula II

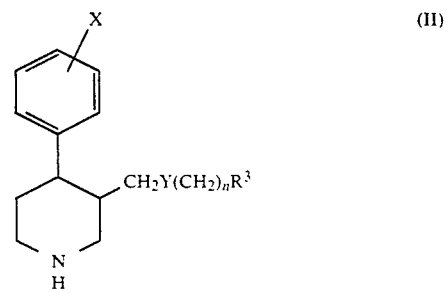

wherein X, Y, n and $R^3$ have the meanings defined above, with a compound having the general formula $R^1$-Z, wherein Z is a leaving group such as e.g. halogen or sulfonates and $R^1$ has the meaning defined above; or b) reacting a compound having the formula III

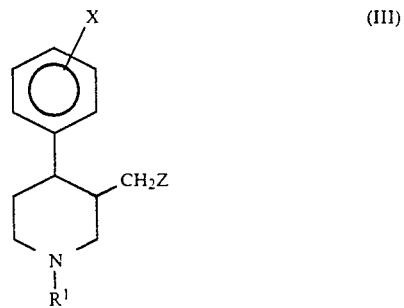

wherein X and $R^1$ have the meanings defined above, and Z is a leaving group such as e.g. halogen or sulfonates, with a compound having the general formula $R^3(CH_2)_nYH$, wherein n, Y and $R^3$ have the meanings defined above; or c) reacting a compound having the formula IV

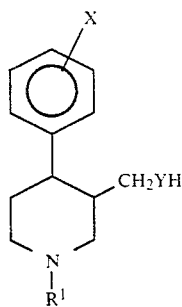

(IV)

wherein Y is O or NR; X, R and $R^1$ have the meanings defined above, with an activated aromatic fluorine compound by means of NaH or alkoxide in dimethylformamide or dimethylacetamide.

The preparation of compounds of formula IV proceeds by procedures described in European patent appl. nos. EP-A-374674 and EP-A-374675 and in U.S. Pat. Nos. 4,861,893 and 4,902,801 with proper modification of the substitution pattern. Compounds III are prepared from IV by known chemical procedures.

The pharmacological properties of the compounds of the invention can be illustrated by determining their capability to inhibit calcium uptake into brain synaptosomes.

PRINCIPLE

Depolarization of neuronal membranes leads to an opening of socalled "voltage operated calcium channels" (VOC) in the membranes which allows a massive influx of calcium from the extracellular space. A crude synaptosomal preparation (socalled $P_2$ fraction) contains small vesicles surrounded by neuronal membrane and it is possible in such a preparation to study a depolarization-induced opening of VOC. In the present model $^{45}Ca$ influx is induced in the synaptosomes by depolarization with elevated potassium concentrations, and the effect of test substances on this stimulated uptake is studied (Nachshen, D. A. and Blaustein, M. P., Mol. Pharmcol., 16, 579 (1979)).

ASSAY

A male Wistar rat is decapitated and the cerebral cortex removed and homogenized in 10 ml. of ice-cold 0.32M sucrose using a glass homogenizer with a teflon pestle. All subsequent steps for isolation of synaptosomes are done at 0°–4° C. The homogenate is centrifuged at 1000×g for 10 min and the resulting supernatant is re-centrifuged at 18000×g for 20 min. This pellet ($P_2$) is resuspended in 0.32M sucrose (5 ml per g of original tissue) with a teflon pestle.

Aliquots (0.050 ml) of this crude synaptosomal suspension are added to glass tubes containing 0.625 ml of NaCl buffer (136 mM NaCl, 4 mM KCl, 0.35 mM $CaCl_2$, 1.2 mM $MgCl_2$, 20 mM Tris HCl, 12 mM glucose, pH 7.4) and 0.025 ml of various drug solutions in 48% Ethanol. The tubes are pre-incubated for 30 min on ice and then for 6 min at 37° C. in a water bath.

The uptake is immediately initiated by adding 0.4 ml of $^{45}CACl_2$ (specific activity=29–39 Ci/g; 0.5 µCi/assay), in 145 mM NaCl for non-depolarized samples and in 145 mM KCl for depolarized samples. The incubation is continued for 15 s.

The uptake is terminated by rapid filtration through GF-C glass fiber filters which are washed three times with 5 ml of a cold solution containing 145 mM KCl, 7 mM EGTA and 20 mM Tris HCl, pH 7.4. The amount of radioactivity on the filter disc is determined by liquid scintillation spectrometry.

TEST PROCEDURE

Test substances are dissolved in 10 ml of 48% ethanol at a concentration of 0.44 mg/ml. Dilution are made in 48% ethanol to give final concentrations of 0.1, 0.3, 1, 3 and 10 µg/ml. Experiments are performed in triplicate. Controls for depolarized and nondepolarized samples are included in the assay and test substances are only tested in depolarized samples. 25–75% inhibition of stimulated uptake must be obtained before calculating the $IC_{50}$ value.

RESULTS

The test value will be given as $IC_{50}$ (the concentration (µg/ml) of test substance which inhibit 50% of stimulated uptake of $^{45}Ca$ (uptake in depolarized samples corrected for basal uptake in nondepolarized samples )). The $IC_{50}$ value is estimated from dose response curves.

Test results obtained by testing some compounds of the present invention will appear from the following table 1

TABLE 1

| Compound | $IC_{50}$ (µg/ml) |
| --- | --- |
| 9 | 7.2 |
| 10 | 8.9 |
| 11 | 4.9 |
| 15 | 5.0 |
| 17 | 7.4 |
| 20 | 2.7 |
| 22 | 4 |
| 60 | 5.5 |
| 36 | 6.4 |
| 51 | 3.8 |
| 52 | 2.8 |
| 57 | 3.2 |
| 64 | 4.2 |
| 65 | 6.5 |
| *Nifedipine | 26 |
| *Verapamil | 16 |
| *Diltiazem | >90 |
| *Flunarizine | 20 |

*well known calcium antagonists.

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets of filled capsules, or liquids, such as solutions, suspensions, emulsions, elixirs, or capsules filled with the same, all for oral use, in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective calcium overload blocking amount of the active ingredient commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir of the like can be used in cases where a sweetened vehicle can be employed.

Generally, the compounds of this invention are dispensed in unit form comprising 0.05-100 mg in a pharmaceutically acceptable carrier per unit dosage.

The dosage of the compounds according to this invention is 0.1-300 mg/day, preferably 10-100 mg/day, when administered to patients, e.g. humans, as a drug.

A typical tablet which may be prepared by conventional tabletting techniques contains:

| Active compound | 5.0 mg |
| Lactosum | 67.8 mg Ph.Eur. |
| Avicel TM | 31.4 mg |
| Amberlite TM IRP 88 | 1.0 mg |
| Magnesii stearas | 0.25 mg Ph.Eur. |

Due to the high calcium overload blocking activity, the compounds of the invention are extremely useful in the treatment symptoms related to an accumulation of calcium in brain cells of mammals, when administered in an amount effective for blocking activity of compounds of the invention includes both activity against anoxia, traumatics injury, ischemia, migraine and epilepsy. The compounds of the invention may accordingly be administered to a subject, e.g., a living animal body, including a human, in need of a calcium overload blocker, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutanous) route, in an effective calcium overload blocking amount, and in any event an amount which is effective for the treatment of anoxia, traumatic injury, ischemia, migraine, epilepsy, or neurodegenerative diseases due to their calcium overload blocking activity. Suitable dosage ranges are 1–200 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples.

EXAMPLE 1

(+)trans-1-methyl-3-(3,4-methylenedioxyphenoxymethyl)-4-(4-nitrophenyl)piperidine, hydrochloride (1)

(−)cis-3-hydroxymethyl-1-methyl-4-(4-nitrophenyl)-piperidine (2) (30 g) was dissolved in dry toluene (400 ml). Triethylamine (24.3 g) and subsequently benzenesulphonyl chloride (25.5 g) were added under stirring. The mixture was stirred at room temperature for 17 h, filtered and washed with 4N NaOH (2×400 ml). The toluene phase was separated, dried with MgSO$_4$ and evaporated to dryness. The resulting mixture was crystallized from methanol. M.p. 122.2–122.8° C., identified by $^1$H NMR as 3-benzenesulphonyloxymethyl-1-methyl-4-(4-nitrophenyl)piperidine (3).

Compound (3) (7.9 g) dissolved in MIBC (200 ml) was added to a solution of sesamol (3.06 g) and NaOH (0.88 g) in MIBC (200 ml). The mixture was stirred 2 h at 130° C. filtered and evaporated to dryness. The residue was evaporated with 3×200 ml toluene to remove residual MIBC. The residue was extracted several times with ether and the combined ether phase was washed with NaOH (4N) and dried. Subsequent evaporation followed by purification on a silica gel column using CH$_2$Cl$_2$/CH$_3$OH 9/1 as eluent gave compound (1) (3.5 g) precipitated as the hydrochloride. M.p. 190°–195° C., identified by $^1$H NMR and MS.

(−)trans-1-methyl-3-(3,4-methylenedioxyphenoxymethyl)-4-(4-nitrophenyl)piperidine, hydrochloride (4)

Was prepared as described for compound (1) using (+)cis-3-hydroxymethyl-1-methyl-4-(4-nitrophenyl)-piperidine as starting material. M.p. 203°–208° C.

(+)trans-1-methyl-4-(4-nitrophenyl)-3-(4-trifluoromethylphenoxymethyl)piperidine, oxalate (5)

(−)cis-3-hydroxymethyl-1-methyl-4-(4-nitrophenyl) piperidine (5 g) was dissolved in DMF (50 ml) and added dropwise to a mixture of NaH (1.06 g) and DMF (50 ml) held at 70° C. After stirring for 30 min at 70° C. 4-fluorobenzotrifluoride (3.57 g) was added and the reaction mixture warmed for 2.5 h at 90° C. After cooling to RT overnight, H$_2$O (100 ml) and toluene (200 ml) was added, and the toluene phase was separated, dried (MgSO$_4$) and evaporated to dryness. The crude product was purified on a silica gel column using CH$_2$Cl$_2$/CH$_3$OH 9/1 as eluent. Compound (5) was precipitated as the oxalate by means of anhydrous oxalic acid in acetone. Identified by $^1$H NMR and MS.

(+)trans-3-(3,4-methylenedioxyphenoxymethyl)-4-(4-nitrophenyl)piperidine, hydrochloride (6)

Was prepared from compound (1) (2.4 g) by treatment with 1-chloroethyl chloroformate (1.02 g) in 1,2- dichloroethane (100 ml) as described by Olofson et. al (J. Org. Chem. 49 (1984) 2081). Rinse up on a silica gel column gave 1.5 g of compound (6). M.p. 95°–100° C.

(+)trans-3-(3,4-methylenedioxyphenoxymethyl)-4-(4-nitrophenyl)-1-pentylpiperidine, hydrochloride (7)

Compound (6) (1 g) was dissolved in abs. ethanol (50 ml). $K_2CO_3$ (0.7 g) and 1-bromopentane (0.63 ml) were added. Reflux for 6 h, filtering and evaporation to dryness gave a crystalline mass which was extracted with NaOH(4N)ether. The etheral layer was dried, evaporated and purified on a silica gel column using $CH_2Cl_2/CH_3OH$ 9/1 as eluent. Precipitated as the hydrochloride from acetone/ether. Yield 0.5 g. M.p. 57° C.

(−)trans-1-methyl-4-(4-nitrophenyl)-3-(3-trifluoromethylphenoxymethyl)piperidine, hydrochloride (8)

Compound (8) was prepared from (+)cis-3-hydroxymethyl-1-methyl-4-(4-nitrophenyl)piperidine as described for compound (1) using 3-trifluoromethylphenol instead of sesamol. The crude product was purified on a silica gel column using $CH_2Cl_2/CH_3OH$ 9/1 as eluent. Identified by $^1H$ NMR. M.p. 271°–272° C.

(31)trans-4-(4-nitrophenyl)-3-(3-trifluoromethylphenoxymethyl)piperidine, hydrochloride (9)

Compound (9) was prepared from compound (8) (3.4 g) as described under the preparation of compound (6). Yield 2.8 g of a hard glass identified as compound (9) by $^1H$ NMR.

EXAMPLE 2

(+)trans-4-(4-aminophenyl)-3-(3,4-methylenedioxyphenoxymethyl)-1-pentylpiperidine, hydrochloride (10)

Compound (7) (0.39 g) in abs. ethanol (50 ml) was hydrogenated at atm. pressure using 5% PdC (50 mg) as catalyst. The reaction mixture was filtered, evaporated to dryness. Extraction with NaOH(4N)-ether, separation of the etheral layer, drying (MgSO$_4$), followed by evaporation to dryness gave an yellow oil which was purified on a silica gel column and precipitated as a very hygroscopic hydrochloride from acetone-ether. Identified by $^1H$ NMR.

EXAMPLE 3

(+ −)trans-1-butyl-4-(4-dimethylaminophenyl)-3-(4-trifluoromethylphenoxymethyl)piperidine, hydrochloride (11)

1-Butyl-3-hydroxymethyl-4-(4-dimethylaminophenyl)piperidine (12) (8.5 g) (prepared from 4-dimethylaminobenzaldehyde and ethyl N-butylamidomalonate analogous to the procedure described in U.S. Pat. No. 4,902,801) was treated with NaH (1.4 g) and 4-fluorobenzotrifluoride (9.6 g) in DMF (150 ml) using the procedure described for the preparation of compound (5). The crude product was purified on a silica gel column giving 11.7 g crystals after precipitation as the hydrochloride. M.p. 223.4°–223.7° C.

(+ −)trans-4-(4-dimethylaminophenyl)-1-(2-methylbutyl)-3-(4-trifluoromethylphenoxymethyl)piperidine, hydrochloride (13)

Was prepared as described for compound (11) from the 1-(2-methylbutyl) analogue of compound (12) (2 g), NaH (0.32 g) and 4-fluorobenzotrifluoride (2.16 g) in DMF (100 ml). 3 g crude product was purified on a silica gel column identified as compound (13) by MS and $^1H$ NMR. M.p. 237.2°–237.6° C.

(+ −)trans-1-butyl-4-(4-dimethylaminophenyl)-3-(2-trifluoromethylphenoxymethyl)piperidine, hydrochloride (14)

Preparation as described for compound (11) using 1 g of compound (12), 2-fluorobenzotrifluoride (1.2 g) and NaH (0.174 g) in DMF (100 ml). The crude product was precipitated as the hydrochloride from acetone-ether giving 0.4 g of crystals. M.p. 213.9°–214.9° C.

(+ −)trans-1-butyl-4-(4-dimethylaminophenyl)-3-(3,4-methylenedioxyphenoxymethyl)piperidine, hydrochloride (15)

3-benzenesulphonyloxymethyl-1-butyl-4-(4-dimethyl-aminophenyl)piperidine (16) (2 g) (prepared from compound (12), benzenesulphonyl chloride and triethylamine by known procedures) was treated with sesamol (0.73 g) and NaOH (0.21 g) in MIBC as described for the preparation of compound (1). Reflux for 2 h. The crude product was purified several times on a silica gel column using $CH_2Cl_2/CH_3OH$ 9/1 as eluent. Yield 0.05 g of colorless crystals after precipitation as the hydrochloride. M.p. 211.5°–214°·C.

(+ −)trans-1-butyl-4-(4-dimethylaminophenyl)-3-(3-trifluoromethylphenoxymethyl)piperidine, hydrochloride (17)

0.4 g of 1-butyl-3-chloromethyl-4-(4-dimethylaminophenyl) piperidine (18) in DMF (25 ml) (prepared from compound (12) by known procedures) was added to a 70° C. hot mixture of 3-trifluoromethylphenol (0.28 g) and NaH (0.09 g) in DMF (25 ml). Reaction time 2 h at 100° C. Evaporation with 3×100 ml toluene. The residue was extracted with NaOH (4N)-ether, the etheral layer separated and dried (MgSO$_4$), purified on a silica gel column and precipitated with concentrated HCl from acetone. Yield 0.22 g of colorless crystals. M.p. 221°–223° C.

(+ −)trans-4-(4-dimethylaminophenyl)-3-(3,4-methylenedioxyphenoxymethyl)-1-(2-methylbutyl)-piperidine, hydrochloride (19)

Was prepared from the crude 1-(2-methylbutyl)-analogue of (18) (3.8 g), NaH (0.81 g) and sesamol (2.13 g) in DMF (50 ml) as described for compound (17). The crude product was purified several times on a silica gel column using ethylacetate and heptane/ether 4/1 as eluents. Compound (19) was identified by $^1H$ NMR and MS. M.p. 238.5°–239.5° C.

EXAMPLE 4

1-butyl-3-(4-methoxybenzylaminomethyl)-4-phenyl-piperidine, HCl (20)

2.5 g (0.6 mmol) 3-(benzensulfonyloxymethyl)-1-butyl-4-phenyl-piperidine (21) was mixed with 825 mg (6 mmol) 4-methoxybenzylamine and heated for 4 h at 90° C. The resulting crystals were washed with $CH_2Cl_2$. The precipitate was stirred in 4N NaOH and extracted with ether. Dried with MgSO$_4$, evaporated in vacuo. The hydrochloride was precipitated from an acetone/ether solution. Yield: 2.3 g.

$^1$H-NMR: 0.8–1.3 (m, 3H); 1.3–2.5 (m, 14H); 2.6–3.3 (m, 2H 3.4 (s, 2H); 3.7 (s, 3H); 6.6–7.2 (m, 9H).

1-butyl-3-(4-trifluoromethylphenylaminomethyl)-4-phenylpiperidine, HCl (22)

2.5 g (0.6 mmol) (21) was added to 965 mg (6 mmol) 4-trifluoromethylaniline. The reaction mixture was heated for 3 h at 90° C. The resulting oil was dissolved in CH$_2$Cl$_2$ and washed with 4N NaOH. Then the oil was washed with 1N HCl and extracted with ether to get rid of some impurity. The water phase was added NaOH. Then extracted with ether. Dried with MgSO$_4$, evaporated in vacuo. The remaining oil was acidified with conc. HCl. Yield: 1.0 g crystals. M.p. 131°–135° C.

1-butyl-3-(4-methoxyphenylaminomethyl)-4-phenyl-piperidine, HCl (23)

2.5 g (6 mmol) of (21) was added to 725 mg (6 mmol) p-anisidine and 5 ml pyridine. The reaction mixture was heated at 100° C. for 3–4 h. The reaction mixture was washed with 4N NaOH and extracted with ether. The ether phase was evaporated stirred in 1N HCl washed with CH$_2$Cl$_2$. The water phase was added solid NaOH, extracted with ether and dried, evaporated in vacuo giving 400 mg oil which was acidified with conc. HCl, giving 600 mg crystals with m.p. 192°–204° C. GC-MS showed that it was a mixture of two isomers 34:64%. M.p. 192°–204° C.

EXAMPLE 5

3-(4-methoxybenzylaminomethyl)-1-methyl-4-phenyl-piperidine, HCl (24)

3.4 g (10 mmol) (21) was mixed with 1.37 g p-methoxybenzylamine. The reaction mixture was refluxed for 2 h, washed with 4N NaOH and extracted with ether. The ether phase was dried with MGSO$_4$ and evaporated in vacuo. The remaining oil (2.1 g) was precipitated with oxalic acid. Yield 2.2 g crystals. M.p. 192°–200° C.

3-(3-fluorobenzylaminomethyl)-1-methyl-4-(4-methoxyphenyl)-piperidine, HCl (25)

1.0 g (4.3 mmol) 3-aminomethyl-4-(4-methoxyphenyl)-1-methyl-piperidine (26) was dissolved in 30 ml EtOH, 2 g K$_2$CO$_3$ and 613 mg (4.3 mmol) 3-fluorobenzylchloride added. The reaction mixture was refluxed for 6 h, filtered and evaporated in vacuo. Addition of ether to the oil precipitated the base. The crude base was chromatographed on a silica gel column with CH$_2$Cl$_2$: MeOH:DEA as eluent. The oil was acidified with conc. HCl. Yield: 72 mg hard glass. M.p. 240° C.

3-(4-fluorobenzylaminomethyl)-1-methyl-4-(4-methoxyphenyl)-piperidine, HCl (27)

1.5 g (6.4 mmol) (26) was dissolved in 50 ml EtOH. 2 g K$_2$CO$_3$ was added together with 925 mg (6.5 mmol) 4-fluorobenzyl chloride. The reaction mixture was refluxed for 6 h. Subsequently the reaction mixture was filtered and evaporated in vacuo. Addition of ether precipitated the base. The crude base was chromatographed on silica gel with CH$_2$Cl$_2$, MeOH, DEA as eluent. The product was precipitated from an acidified ether, acetone solution yielding 260 M.p. 265°–266° C.

3-(2-fluorobenzylaminomethyl)-1-methyl-4-(4-methoxyphenyl)piperidine, HCl (28)

1.0 g (4.3 mmol) (26) was dissolved in 30 ml EtOH. 2 g K$_2$CO$_3$ and 613 mg (4.3 mmol) 2-fluorobenzylchloride were added. The reaction mixture was refluxed for 6 h. Then the reaction mixture was filtered and evaporated in vacuo. Some crystalline compound was obtained by adding ether. The ether phase was washed with acid and subsequently with base, evaporated to dryness, dissolved in acetone then acidified with conc. HCl. The HCl-salt was chromatographed on silica gel with CH$_2$Cl$_2$:MeOH:DEA as eluent. Yield: 110 mg of the HCl-salt. M.p. 251° C.

(+ −)
3-(4-methoxyphenylaminomethyl)-1-methyl-4-phenyl-piperidine, HCl (29)

5 g (14.5 mmol) 3-(benzenesulfonyloxymethyl)-1-methyl-4-phenyl-piperidine (30) was dissolved in 50 ml pyridine and 1.8 g (15 mmol) p-anisidine was added. The reaction mixture was refluxed for 8 h. The pyridine was removed in vacuo. The remaining oil was washed with 4N NaOH and extracted with ether. Dried with MgSO$_4$ and evaporated to dryness giving 1.7 g oil. The oil was chromatographed on a silica gel column with CH$_2$Cl$_2$:MeOH 9:1 as eluent. The compound was crystallized as the HCl-salt. Yield: 190 mg $^1$H-NMR: 1.6–2.2 (m, 6H); 2.4 (s, 3H); 2.6–3.2 (m, 4H); 3.7 (s, 3H); 6.2–6.6 (q, 4H); 7.2 (s, 5H).

(+ −)
trans-1-pentyl-4-phenyl-3-(1,2,3,4-tetrahydro-5-naphthylaminomethyl)-piperidine, HCl (31)

4.3 g (10.7 mmol)3-(benzenesulfonyloxymethyl)-4-phenyl-1-pentyl-piperidine (32) was dissolved in 80 ml toluene-MBC 1:1 0.86 ml pyridine was added. The reaction mixture was heated for 72 h at 80° C. The reaction mixture was evaporated in vacuo. The oil was dissolved in ether and washed with 4N NaOH. The water phase was extracted with ether, dried with MgSO$_4$ and evaporated giving 5 g black oil which was chromatographed on silica gel with CH$_2$Cl$_2$:MeOH 19:1 as eluent. The HCl-salt precipitated from an acidified acetone ether solution. Yield: 34 mg. M.p. 214°–216° C.

(−)
trans-3-(benzylaminomethyl)-1-butyl-4-phenylpiperidine, HCl (33)

1.5 g (3.9 mmol) (−) trans-3-(benzenesulfonyloxymethyl)-1-butyl-4-phenyl-piperidine (34) was mixed with benzylamine (20 ml) and heated for 24 h at 85° C. The reaction mixture was washed with 4N NaOH and extracted with ether. The ether phase was dried with MgSO$_4$ and evaporated in vacuo. The remaining yellow oil (1.3 g) was chromatographed on silica gel with CH$_2$Cl$_2$/MeOH 9:1 as eluent. The di-HCl-salt was recrystallized twice from MeOH/acetone. M.p.>280° C.

EXAMPLE 6

(−) trans
1-butyl-3-(2-phenylethylaminomethyl)-4-phenylpiperidine, HCl (35)

1 g (2.6 mmol) (34) was mixed with 15 ml 2-phenylethylamine and heated for 25h at 85° C. The ether phase was dried with MgSO$_4$ and evaporated in vacuo. 3 g yellow oil was obtained. The oil was purified by chromatography on silica gel with CH$_2$Cl$_2$ MeOH 9:1 as eluent. 1.1 g oil was acidified with conc. HCl and the di-HCl-salt precipitated from acetone/ether. Yield 0.95 g white crystals. M.p. 220°–220.8° C.

EXAMPLE 7

(−) trans-4-(4-fluorophenyl)-1-pentyl-3-(4-trifluoromethyl-benzyloxymethyl)-piperidine, HCl (36)

(+) cis 3-benzenesulfonyloxymethyl-4-(4-fluorophenyl)-1-pentyl piperidine (37) was dissolved in 4-trifluoromethylbenzylalkohol (5 g) and 5 ml toluene. 0.2 g NaH (50%) was added under $N_2$. The reaction mixture was heated for 18h at 65° C. Then it was washed with 4 N NaOH and extracted with ether. The organic phase was dried with $MgSO_4$ and evaporated in vacuo. 1 g yellow oil was chromatographed on a silica gel column with $CH_2Cl_2$:MeOH 9:1 as eluent. Subsequently it was chromatographed with ethyl acetate as eluent. 0.47 g oil was acidified with conc. HCl, 0.5 g white crystals precipitated. M.p. 134.6° C.

(+−) trans-3-(2-(4-methoxyphenoxy)ethoxymethyl)-1-methyl-4-phenylpiperidine, oxalate (38)

8.5 g (2.45 mmol) (30) was dissolved in dry toluene, 4.9 g (2.9 mmol) 2-(4-methoxyphenoxy)ethanol and 1 g NaH was added. The reaction mixture was refluxed under $N_2$ for 34 h. The toluene phase was washed with 4 N NaOH and extracted with ether. The organic phase was dried with $MgSO_4$ and evaporated in vacuo. 8.1 g yellow oil was chromatographed on silica gel column with $CH_2Cl_2$:MeOH 9:1 as eluent.

The oxalate was a hard glass. M.p. 35°–57° C.

(+−) trans-3-(2-(4-methoxyphenoxy)ethoxymethyl)-4-phenylpiperidine, oxalate (39)

3.7 g (1.04 mmol) (38) as the free base was dissolved in dry toluene under $N_2$. 2.23 g (1.56 mmol) 1-chloroethyl chloroformate was dropped slowly to the ice-cooled reaction mixture. Then the reaction mixture was refluxed for 5h. 20 ml MeOH was added and refluxed further for 1h. Evaporation in vacuo gave a brown oil which was washed with 4N NaOH and extracted with $CH_2Cl_2$. Dried with $MgSO_4$ and evaporation gave 3.6 g oil, which was chromatographed on a silica gel column with $CH_2Cl_2$/MeOH 9:1 as eluent. The oxalate precipitated from acetone/ether. Yield 3.1 g. M.p. 138.8°–140.8° C.

(+−) trans-3-(2-(4-methoxyphenoxy)ethoxymethyl)-1-pentyl-4-phenyl-piperidine, oxalate (40)

2.15 (5 mmol) (39) was dissolved in 50 ml EtOH. 4 g $K_2CO_3$ was added together with excess pentyl bromide. The reaction mixture was heated for 18 h at 60° C. Filtration and evaporation in vacuo. The oil was washed with 4 N NaOH and extracted with ether. The ether phase was treated with charcoal and dried with $MgSO_4$. The residue after evaporation was chromatographed on a silica gel column with $CH_2Cl_2$ MeOH (9:1) as eluent. 1.15 g oil was treated with oxalic acid. Yield 1.2 g. M.p. 123°–125° C.

EXAMPLE 8

(+−) trans 4-(4-dimethylaminophenyl)-3-(4-trifluoromethyl-phenoxymethyl) piperidine, hydrochloride (41)

Was prepared from compound (13) (3 g) and 1-chloroethyl chloroformate (1 g) in dry 1,2-dichloroethane (50 ml) as described for compound (6). Yield 62%. M.p. 195.5°–199.6° C. (d).

(+−) trans 4-(4-dimethylaminophenyl)-1-ethyl-3-(4-trifluoromethylphenoxymethyl) piperidine, hydrochloride (42)

Was prepared from (41) (0.35 g) and ethyl iodide (0.4 g) in abs. ethanol (30 ml). heating to 60° C. for 8 h, and subsequently at room temperature for 48 h in the presence of $K_2CO_3$ (0.4 g). Purification as described for compound (7) gave a yield of 38% of (42). M.p. 225.8°–228.1° C.

(+−) trans 4-(4-dimethylaminophenyl)-1-propyl-3-(4-trifluoromethylphenoxymethyl) piperidine, hydrochloride (43)

Preparation from (41) (0.35 g) and 1-iodopropane (0.2 ml) by heating in ethanol of 70° C. for 8 h, as described for compound (42). Yield 37%, m.p. 224.2°–225.2° C.

EXAMPLE 9

(+−) trans 4-(4-diethylaminophenyl)-1-(2-methyl-butyl)-3-(4-trifluoromethylphenoxymethyl) piperidine hydrochloride (44)

Was prepared from 4-(4-diethylaminophenyl)-3-hydroxymethyl-1-(2-methylbutyl) piperidine (45) and 4-fluorobenzotrifluoride as described for compound (11). Compound (45) was prepared from ethyl N-(2-methylbutyl)amidomalonate and 4-diethylaminobenzaldehyde as described above. Yield of (46) 50%. M.p. 250.7°–250.9° C.

(+−) trans 4-(4-diethylaminophenyl)-3-(4-trifluoromethyl phenoxymethyl) piperidine, hydrochloride (46)

Preparation by dealkylation of (44) as described for compound (41). Yield 23%. M.p. 220.5°–227.6° C.

EXAMPLE 10

3-benzenesulfonyloxymethyl-1-butyl-4-dimethylaminophenyl piperidine (47)

Was prepared from (12) and benzenesulphonyl chloride as described under the preparation of compound (1). The crude product, identified by $^1H$ NMR and shown by HPLC to be more than 80% pure, was used for the preparation of the following compounds by adding a solution of (47) in DMF to a mixture of the appropriate phenol and NaH in DMF. Stirring at RT or under heating until complete consumption of (47) could be proved by HPLC. Subsequently the mixture was evaporated to dryness and the product was isolated using the purification procedure described for the preparation of compound (1).

(+−) trans 1-butyl-4-(4-dimethylaminophenyl)-3-(5,6,7,8-tetrahydro-2-naphthoxymethyl) piperidine, hydrochloride (48)

From (47) (1 g) and 5,6,7,8-tetrahydro-2-naphthol (0.45 g) by heating for 2 h. Yield 18%. M.p. 216.7°–2176.6° C.

(+−) trans 1-butyl-4-(4-dimethylaminophenyl) 3-(3-methylphenoxymethyl) piperidine, hydrochloride (49)

From (47) (1 g) and 3-methylphenol (0.33 g) by heating for 2.5 h. Yield 21%, m.p. 230.2°–230.9° C.

(+−) trans
1-butyl-4-(4-dimethylaminophenyl)3-(4-fluorophenoxymethyl) piperidine, hydrochloride (50)

From (47) (1 g) and 4-fluorophenol (0.34 g) by heating for 2 h. Yield 35%, m.p. 225.5° C. (d).

(+−) trans
1-butyl-3-(4-chlorophenoxymethyl)-4-(4-dimethylaminophenyl) piperidine, hydrochloride (51)

From (47) (1 g) and 4-chlorophenol (0.39 g) by standing at room temperature overnight. Yield 34%, m.p. 211.1° C. (d).

(+−) trans 1 -butyl-3-(3,4-dichlorophenoxymethyl) 4-(4-dimethylaminophenyl) piperidine, HCl (52)

From (1 g) (47) and 3,4-dichlorophenol (0.5 g) by standing at room temperature overnight. Yield 15%, m.p. 234.2°–234.6° C.

(+−) trans
1-butyl-3-(2-cyanophenoxymethyl)-4-(4-dimethylaminophenyl) piperidine, HCl (53)

From (47) (1 g) and 2-cyanophenol (0.36 g) by standing overnight at room temperature. Yield 8%. M.p. 200°–201° C.

(+−) trans 1-butyl-4-(4-dimethylaminophenyl) 3-(3-nitrophenoxymethyl) piperidine, HCl (54)

From (47) (1 g) and 3-nitrophenol (0.48 g) by standing at room temperature overnight. Yield 3%. M.p. 236°–237° C.

(+−) trans 1-butyl-3-(3-cyanophenoxymethyl) 4-(4-dimethylaminophenyl) piperidine, HCl (55)

From (47) (1 g) and 3-cyanophenol (0.36 g) by standing at room temperature for 24 h. Yield 12%. M.p. 237.2°–238.8° C.

(+−) trans
1-butyl-4-(4-cyanophenoxymethyl)-4-(4-dimethylaminophenyl) piperidine, HCl (56)

From (47) (1 g) and 4-cyanophenol (0.36 g) by standing at room temperature for 48 h. Yield 21%, m.p. 179°–181° C.

(+−) trans
1-butyl-4-(4-dimethylaminophenyl)-3-(4-nitrophenoxymethyl) piperidine, HCl (57)

From (47) (1 g) and 4-nitrophenol (0.48 g) by standing overnight at room temperature. Yield 3%, m.p. 215.5° C. The compound was somewhat contaminated with 1-butyl-3-chloromethyl-4-(4-dimethylaminophenyl) piperidine, HCl.

EXAMPLE 11

(−)trans-3-(benzyloxymethyl)-4-(4-fluorophenyl)-1-pentylpiperidine, HCl (58)

1 g (0.0024 mol) (+) cis-3(benzenesulfonyloxymethyl)-4-(4-fluorophenyl)-1-pentyl-piperidine (59) was stirred in benzyl alcohol (10 ml) 0.2 g (0.004 mol) NaH was added under $N_2$. The reaction mixture was heated for 16 h at 65° C.

The remaining benzyl alcohol was removed in vacuo. The oil was chromatographed on a silica gel column with $CH_2Cl_2$/MeOH (9:1) as eluent. 0.65 yellow oil was acidified by conc. HCl. The HCl salt was recrystallized from ethyl acetate. M.p. 138°–139° C.

(−)trans-4-(4-fluorophenyl)-1-pentyl-3-(3-trifluoromethylbenzyloxymethyl)-piperidine, HCl (60)

The compound was prepared in the same manner as described for (58). Yield 230 mg oxalate. M.p. 80°–80.2° C.

(−)trans-4-(4-fluorophenyl)-1-pentyl-3-(2-trifluoromethylbenzyloxymethyl)-piperidine, HCl (61)

The compound was prepared in the same manner as described for (58). Yield 200 mg HCl-salt. M.p. 56.7°–57° C.

EXAMPLE 12

(+)-trans-1-butyl-4-(4-dimethylaminophenyl)-3-(4-trifluoromethylphenoxymethyl)piperidine
(−)-di-p-toluoyltartrate (62)

(±)-trans-1-butyl-3-hydroxymethyl-4-(4-dimethylaminophenyl)piperidine (50 g) was dissolved in dry dimethyl formamide (200 ml). Potassium tert-butoxide (23.3 g) was added to the solution and the mixture was stirred at room temperature for 15 min. 4-Fluorobenzotrifluoride (26.4 ml) was added and the mixture was stirred for 1 h. Water (300 ml) was added and the mixture extracted three times with toluene (600 ml). The toluene extract was extracted with water (200 ml), dried over potassium carbonate and evaporated under reduced pressure giving a yellow oil (75.8 g). The oil was dissolved in acetone (400 ml) at 50° C. and (−)-p-ditoluoyltartaric acid (70.6 g) was added. The solution was stirred for 1 h cooled in an ice bath and the precipitate filtered off. Washed with acetone and dried. Yield 68.2 g. M.p. 118°–120° C.

(−)-trans-1-butyl-4-(4-dimethylaminophenyl)-3-(4-trifluoromethylphenoxymethyl)piperidine
(+)-di-p-toluoyltartrate (63)

The filtrate from the preparation of (62) was evaporated, redissolved in dichloromethane (450 ml), extracted with excess saturated sodium carbonate solution. The dichloromethane phase was extracted with water (300 ml), dried over magnesium sulfate and evaporated under reduced pressure. Yield 44.2 g. The residue was dissolved in acetone (350 ml) at 50° C. (+)-p-ditoluoyltartaric acid (39.3 g) was added. The mixture was stirred overnight, cooled in ice-water, the precipitate filtered off, washed with acetone and dried. Yield 61.4 g, m.p. 118°–140° C.

(±)-trans-1-butyl-4-(4-dimethylaminophenyl)-3-(4-trifluoromethylphenoxymethyl)piperidine dihydrochloride (11)

The piperidine base was prepared as described above from (±)-trans-1-butyl-3-hydroxymethyl-4-(4-dimethylaminophenyl)piperidine and 4-fluorobenzotrifluoride in dimethyl formamide with potassium tert-butoxide. The dihydrochloride was precipitated from an acetone solution by addition of 2.2 equivalents of conc. hydrochloric acid. The filtrate was evaporated at reduced pressure and the residue redispensed in acetone giving in all about 90% of the dihydrochloride. M.p. 211°–215° C.

(+)-trans-1-butyl-4-(4-dimethylaminophenyl)-3-(4-tri-fluoromethylphenoxymethyl)piperidine dihydrochloride (64)

The piperidine base was liberated from the (−)-p-ditoluoyltartrate salt (62) (68 g) by extraction of a dichloromethane suspension (500 ml) with saturated sodium carbonate. Sodium carbonate was added until pH was 9.45. The dichloromethane phase was separated, washed with water (200 ml), dried over magnesium sulphate and evaporated under reduced pressure. The dihydrochloride was precipitated from an acetone solution (400 ml) by addition of conc. hydrochloric acid (14.2 ml). Yield 34.9 g. The product was recrystallized from 140 ml acetone and 40 ml methanol. Yield 21.3 g, m.p. 215°–216° C., $[\alpha]^{20}_D = +68.62°$ C.

(−)-trans-1-butyl-4-(4-dimethylaminophenyl)-3-(4-tri-fluoromethylphenoxymethyl)piperidine dihydrochloride (65)

The piperidine base was liberated from the (+)-p-ditoluoyl salt (63) (61.4 g) as described above for the (+)-isomer and isolated as the dihydrochloride. Yield 29.7 g. The product was recrystallized from a mixture of 120 ml acetone and 38 ml methanol. Yield 29.1 g, m.p. 215°–215.8° C., $[\alpha]_D^{20} = -68.66°$ C.

EXAMPLE 13

The following compounds were prepared from compound (41) and an alkylhalide by reflux in abs. ethanolic solution under the presence of $K_2CO_3$ as described for compound (42). Rinse up as described for compound (7).

(+−) trans 1-cyclopropylmethyl-4-(4-dimethylaminophenyl)-3-(4-trifluoromethylphenoxymethyl)piperidine, hydrochloride (66)

Was prepared from (41) (1 g) cyclopropylmethyl bromide (1.17 g) and $K_2CO_3$ (1 g) reflux for 11 h yield 59% of (66). M.p. 211.3°–212.5° C.

(+−) trans 1-allyl-4-(4-dimethylaminophenyl)-3-(4-trifluoromethylphenoxymethyl)piperidine, hydrochloride (67)

From (41) (1 g), allylbromide (0.35 g) and $K_2CO_3$ (1 g). Heating to 50° C. for 4 h. Yield of (67) 35%. M.p. 211.0°–212.8° C.

(+−) trans 1-cyclopentyl-4-(4-dimethylaminophenyl)-3-(4-trifluoromethylphenoxymethyl)piperidine, hydrochloride (68)

Prepared from (41) (1.5 g), bromocyclopentane (0.80 g) and $K_2CO_3$ (1 g). Reflux for 21 h. Purification of the crude product on silica gel column. Yield of (68) 11%. M.p. 205.8°–206.2° C.

(+−) trans 4-(4-dimethylaminophenyl)-1-(3-methylbutyl)-3-(4-trifluoromethylphenoxymethyl)piperidine, hydrochloride (69)

Prepared from (41) (0.5 g), 3-methyl-1-bromobutane (0.4 g) and $K_2CO_3$ (0.5 g). Reflux for 8 h. Purification on silica gel. Yield of (69) 51%. M.p. 223.9°–225.1° C.

(+−) trans 1-acetyl-4-(4-dimethylaminophenyl)-3-(4-trifluoromethylphenoxymethylpiperidine), hydrochloride (70)

Mixing of (41) (0.5 g) with acetylchloride (0.5 ml), 2-bromopropane (0.5 ml) and $K_2CO_3$ (0.5 g) with subsequent heating to 70° C. for 4 days and purification on a silica gel column gave 0.08 g of (70) identified by $^1H$, $^{13}C$ NMR and MS. M.p. 188.4°–190.0° C.

(+−) trans 4-(4-dimethylaminophenyl)-1-isopropyl-3-(4-trifluoromethylphenoxymethyl)piperidine, hydrochloride (71)

0.32 g (71) was isolated from the crude mixture from the preparation of (70). M.p. 227.0°–229.0° C.

(+−) trans 4-(4-dimethylaminophenyl)-1-(2-propynyl)-3-(4-trifluoromethylphenoxymethyl)piperidine, hydrochloride (72)

From (41) (0.5 g), 2-bromo-1-propyn (0.31 g) and $K_2CO_3$ (0.5 g). Reflux for 2 days. Purification on a silica gel column. Yield of (72) 20%. M.p. 198.0°–199.2° C.

EXAMPLE 14

The following compounds were prepared using the method described for the preparation of compounds (47) and (48).

(+−) trans 1-butyl-4-(4-dimethylaminophenyl)3-(4-methylphenoxymethyl)piperidine, hydrochloride (73)

From (47) (1 g) and 4-methylphenol (0.33 g) by standing at RT overnight, yield of (73) 21%. M.p. 216.0°–218.0° C.

(+−) trans 1-butyl-4-(4-dimethylaminophenyl)-3-(2-methylphenoxymethyl)piperidine, hydrochloride (74)

From (47) (1 g) and 2-methylphenol (0.33 g) by standing at RT overnight. Purification on silica gel column using $CH_2Cl_2/CH_3OH$ (9/1) and pentane/triethyl amine (15/1) as eluents. Yield of (74) 21%. M.p. 130°–131° C.

(+−) trans 1-butyl-4-(4-dimethylaminophenyl)-3-(4-trifluoromethoxyphenoxymethyl)piperidine, hydrochloride (75)

From (47) (1 g) and 4-trifluoromethoxyphenol (0.54 g) by standing at RT overnight. Purification on silica gel. Yield of (75) 0.1 g. M.p. 171°–185° C.

EXAMPLE 15

(+−) trans 4-(4-aminophenyl)-1-butyl-3-(4-trifluoromethyl phenoxymethyl)piperidine, hydrochloride (76)

(+−) trans 4-(4-aminophenyl)-1-butyl-3-hydroxymethyl piperidine (77) (2.4 g), 4-trifluoromethylphenol (1.49 g), triphenylphosphine (2.4 g) and diethyl azodicarboxylate (1.6 g) were reacted in dry THF according to the method described by O. Mitsunobu (Synthesis 1981, 1). After reaction at RT for 3 days the solvent was evaporated, the residue extracted with 4M $OH^-$ ether and the dried evaporated ether phases were purified on silicagel (eluent $CH_2Cl_2/CH_3OH$ 9/1) yield of (76) 59%. M.p. 189°–191° C.

(+ −) cis
1-butyl-4-(4-nitrophenyl)-3-(4-trifluoromethylphenoxymethyl) piperidine, hydrochloride (78)

was prepared from (+ −) cis 1-butyl-3-hydroxymethyl-4-nitrophenylpiperidine (12.6 g) analogous to the preparation of (76). Yield of (78) 33% as a hard glass identified by $^1$H and $^{13}$C NMR.

(+ −) trans
1-butyl-4-(4-formylaminophenyl)-3-(4-trifluoromethylphenoxymethyl) piperidine, hydrochloride (79)

Compound (76) (1 g) was dissolved in ethyl formate (10 ml) reflux for 1 h followed by addition of 1M NaOH to pH 5. Heating to 50° C. overnight followed by evaporation to dryness. The residue was partitioned between $CH_2Cl_2/OH^-$, the organic layer dried, evaporated to dryness and precipitated as the hydrochloride from acetone/ether. Yield 45% of (79). M.p. 165°–170° C.

(+ −) trans
1-butyl-4-(4-N-ethyl-N-methylaminophenyl)-3-(4-trifluoromethylphenoxymethyl)piperidine, hydrochloride (80)

(79) (2.7 g) was dissolved in dioxan (50 ml). NaBH$_4$ (0.71 g) and CH$_3$COOH (1.12 g) was added (at 14° C.). Reflux for 8 h. The solvent was evaporated and the residue purified on a silica gel column using $CH_2Cl_2/CH_3OH$ (9/1) as eluent. 0.22 g (80) was isolated. M.p. 236°–237° C. In addition to (80) the following two compounds were isolated.

(+ −) trans
1-butyl-4-(4-ethylaminophenyl)-3-(4-trifluoromethylphenoxymethyl)piperidine, hydrochloride (81)

0.11 g. M.p. 130°–135° C. dec.

(+ −) trans
1-butyl-4-(4-methylaminophenyl)-3-(4-trifluoromethylphenoxymethyl)piperidine, hydrochloride (82)

Yield 0.45 g. M.p. 180° C. dec.

(+ −) trans
4-(4-acetamidophenyl)-1-butyl-3-(4-trifluoromethylphenoxymethyl)piperidine, hydrochloride (83)

(76) (0.5 g) was dissolved in toluene (30 ml) acetyl chloride (176 µl) and triethyl amine (0.5 ml) were added. Stirring at RT for 3 h. 4 M NaOH was added and the mixture extracted with 2×toluene. The combined organic phases was evaporated and the residue precipitated as the hydrochloride from acetone/ether. Yield 0.52 g of (83). M.p. 212°–214° C.

(+ −) trans
1-butyl-4-(4-succinimidophenyl)-3-(4-trifluoromethylphenoxymethyl)piperidine, hydrochloride (84)

(76) (0.6 g) and succinic anhydride (0.15 g) were mixed in toluene. Heating to 160° C. for 2 h after evaporation of the solvent. Cooling to RT, addition of abs. ethanol and subsequent heating to reflux until complete dissolution. Evaporation gave a yellow oil which was purified on silica gel (3 times) yield 50% of (84) M.p. 151.5°–152° C. after precipitation as hydrochloride salt.

(+ −) trans
1-butyl-4-(4-methylsulfonylamidophenyl)-3-(4-trifluoromethylphenoxymethyl)piperidine, hydrochloride (85)

(76) (0.5 g) was dissolved in toluene (30 ml) methanesulfonyl chloride (0.3 g) and triethyl amine (0.5 ml) were stirred at RT overnight. Extraction with $OH^-$/ether/toluene. The organic phases were collected, dried over MgSO$_4$, and evaporated. Purification on silica gel gave 27% of (85). M.p. 130°–135° C. decomp.

1-butyl-4-(4-morpholinophenyl)-3-(4-trifluoromethylphenoxymethyl)piperidine, hydrochloride (86)

(76) (0.7 g), bis-(2,2 dichloroethyl)ether (0.2 ml) and K$_2$CO$_3$ (1 g) were dissolved in abs. ethanol, crystals of I$_2$ and KI were added and the mixture refluxed for 1 week. Evaporation was followed by partition between OH and ether and evaporation of the organic phase gave a yellow oil which was purified on silica gel. 0.3 g of (86) was isolated. M.p. 105° C. dec.

1-butyl-4-(4-N'-ethylureidophenyl)-3-(4-trifluoromethylphenoxymethyl)piperidine, hydrochloride (87)

(76) (0.46 g) was dissolved in touene (30 ml) ethyl isocyanate (250 µl) was added. Stirring at RT for 2 days. Evaporation to dryness followed by extraction with 4 M NaOH/ether. The ether phases were combined, dried, evaporated and the residue precipitated as the hydrochloride salt. Yield of (87) 96%. M.p. 197.0°–198.4° C.

(+ −) trans
4-(4-dimethylaminophenyl)-1-methyl-3-(4-trifluoromethylphenoxymethyl)piperidine, hydrochloride (88)

(41) (1 g) and formic acid (0.56 ml) were mixed in abs. ethanol at 0° C. Formaldehyde (0.25 g 35% solution) was added. The mixture was stirred at RT overnight and heated to 80° C. for 7 h. Addition of further formic acid (0.23 ml) was followed by heating to 80° C. for 20 h. Evaporation of the mixture was followed by extraction of the residue with NaOH(4M)/ether. The etheral layer was evaporated and the residue was purified on silica gel and subsequently precipitated from acetone/ether as the hydrochloride. Yield 33%. M.p. 238°–239.6° C.

EXAMPLE 16

(−) trans
4-(4-fluorophenyl)-1-pentyl-3-(2-trifluoromethylbenzyloxymethyl)piperidine, hydrochloride (89)

(37) (1 g) was reacted with 2-trifluoromethylbenzyl alcohol (1 g) as described for compound (36). Yield 8% of (89).
M.p. 87°–88° C.

(−) trans
3-benzyloxymethyl-4-(4-fluorophenyl)-1-pentylpiperidine, hydrochloride (90)

(37) (1 g) was reacted with benzyl alcohol (1.5 g) and NaH (0.2 g). Heating to 70° C. overnight was followed by rinse up as described for (36) and gave 0.5 g (90). M.p. 142.8°–143.1° C.

(−) trans 1-butyl-3-(4-methoxybenzylaminomethyl)-4-phenyl-piperidine, hydrochloride (91)

(−) trans (21) (2 g) was reacted with 4-methoxybenzyl amine (0.66 ml) by heating at 90° C. for 1 h. The crude product was purified on silica gel using ethyl acetate/triethyl amine 10/1 as eluent. Yield of (91) 0.5 g. M.p. 260°–262° C.

(+−) cis 1-butyl-3-(4-methoxybenzylaminomethyl)-4-phenyl-piperidine, hydrochloride (92)

(+−) cis (21) (0.3 g) was heated with 4-methoxy benzyl amine (0.1 ml) at 70° C. for 6 h. Purification on column as described for (91) yield of (92) 0.025 g.

EXAMPLE 17

(+−) trans 4-(4-trifluoromethyl)-3-hydroxymethyl-1-pentylpiperidine (93)

231 mmol of trans 4-trifluoromethylcinnamic acid was converted to 4-trifluoromethylcinnamoyl chloride by reflux with 577 mmol thionyl chloride in chloroform, and the solvents was subsequently evaporated. The cinnamoyl chloride in 100 ml methylene chloride was slowly added to a suspension of 231 mmol 1-pentyl amine and 138 mmol potassium carbonate in 250 ml methylene chloride under reflux. After 60 min another 231 mmol of 1-pentyl amine was added, refluxing was continued for 60 min, and the reaction mixture left at room temperature overnight. 500 ml methylene chloride was added, and washings with water aqeuous acid and base, followed by evaporation from toluene afforded 4-trifluoromethylcinnamoyl-N-pentylamide 48 g. M.p. 114.5°–114.8° C.

105 mmol 4-trifluoromethylcinnamoyl-N-pentylamide, 116 mmol diethyl malonate, and 285 mmol sodium ethoxide were refluxed in a 1:1 touene/diglyme mixture for 7 h, cooled and washed with dilute HCl and water. Evaporation at 2 torr gave a dark red oil, which was purified by column chromatography on silica to give 23 g 4-(4-trifluoromethyl-phenyl)-3-ethoxycarbonyl-1-pentylpiperidine-2,6-dione as a reddish oil. 57 mmol 4-(4-trifluoromethylphenyl)-3-ethoxycarbonyl-1-pentylpiperidine-2,6-dione in 100 ml THF was slowly added with stirring to a suspension of 260 mmol LiAlH$_4$ in 100 ml THF maintaining the temperature at 10° C., followed by stirring at room temperature overnight. Excess hydride was destroyed by addition of water, followed by 500 ml 4 N HCl. The THF was removed by evaporation, the aqueous phase was extracted by methylene chloride, and the organic phase was washed with 4 N NaOH, dried, and evaporated. Column chromatography on silica yielded the pure compound, which was crystallized from EtOAc. Compound (93). Yield 3.7 g. M.p. 112°–115° C.

(+−) trans 4-(3-trifluoromethyl)-3-hydroxymethyl-1-pentylpiperidine (94)

This compound was prepared from 3-trifluoromethylcinnamic acid in the same manner as described above for the 4-isomer. Compound (94). Yield 2.9 g. M.p. 125°–126° C.

EXAMPLE 18

(+−) trans 4-(4-bromophenyl)-3-(ethoxycarbonyl)-1-pentyl-2,6-piperidinedione (95)

This compound was prepared essentially as described in U.S. Pat. No. 4,902,801. 540 mmol 4-bromobenzaldehyde in 500 ml EtOAc was slowly added to a suspension of 1351 mmol sodium ethylate in 500 ml EtOAc with stirring, maintaining the temperature below 10° C. Stirring was continued for one hour while the temperature was allowed to increase to room temperature. A solution of 648 mmol ethyl-N-pentylamidomalonate in 250 ml EtOAc was slowly added, and the stirring continued for 3 days. 360 ml of 25% acetic acid in water was added, and the organic phase was washed with brine and evaporated. Re-evaporation from 500 ml of toluene gave a mass which was crystallized from 1400 ml of 80% EtOH in water. Compound (95) yield 150. M.P. 61°–65° C.

(+−) trans 4-(4-bromophenyl)-3-(hydroxymethyl)-1-pentylpiperidine (96)

244 mmol (+−) trans 4-(4-bromophenyl)-3-(ethoxycarbonyl)-1-pentyl-2,6-piperidine-dion in 500 ml dry THF, was dropwise added to a suspension of 448 mmol LiAlH$_4$ in 500 ml THF, with stirring and maintaining the temperature at −20° C. Stirring was continued at −20° C. for 1 h, and then at room temperature overnight. Residual hydride was destroyed by addition of water, followed by 350 ml 6N HCl. The phases were separated, and the aqueous phase extracted by 4×250 ml methylene chloride. The organic phases were combined and evaporated. Dried by re-evaporation from toluene, and triturated by ether. The product was released from the hydrochloride by partitioning between methylene chloride and 2N NaOH, and recrystallized from EtOAc. Compound (96) yield 35 g. M.p. 128°–130° C.

The following compounds were prepared essentially in the same manner. The cooling to −20° C., during the addition to the LiAlH$_4$-suspension, was only employed with the bromo compounds, the other diones were reduced at 10° C. None of the diones were crystallized. Instead the oils obtained from the evaporation were dissolved in toluene, dried with K$_2$CO$_3$, and reduced without further purification.

(+−) trans 4-(3-bromophenyl)-3-hydroxymethyl-1-butylpiperidine (97)

From 50 g 3-bromobenzaldehyde. Compound (97) yield 25 g.

(+−) trans 4-(2-bromophenyl)-3-hydroxymethyl-1-pentylpiperidine (98)

From 15 g 2-bromobenzaldehyde. Compound (98) yield 7.36 g. M.p. 119°–120° C.

(+−) trans 4-(2-trifluoromethylphenyl)-3-hydroxymethyl-1-pentylpiperidine (99)

From 20 g 2-trifluoromethylbenzaldehyde. Compound (99) yield 14.29 g. M.p. 109.5°–110° C.

(+−) trans
4-(2-chlorophenyl)-3-hydroxymethyl-1-pentylpiperidine (100)

From 10 g 2-chlorobenzaldehyde. Compound (100) yield 8.89 g. M.p. 101°–102° C.

(+−) trans
4-(4-chlorophenyl)-3-hydroxymethyl-1-pentylpiperidine (101)

From 10 g 4-chlorobenzaldehyde. Compound (101) yield 5.48 g. M.p. 125°–128° C.

EXAMPLE 19

(+−) trans
4-(4-bromophenyl)-3-(4-trifluoromethylphenoxymethyl)-1-pentylpiperidine, HCl (102)

73.5 mmol of compound (96) and 147 mmol 4-trifluoromethylfluorobenzene was dissolved in 250 ml dry DMF and poured over 81 mmol of potassium tert-butoxide, with vigorous stirring and while cooled in an ice/water bath. Stirring was continued for 30 min. at room temperature, and then the solution was poured into a mixture of 1000 ml ice/water and 750 ml ether. Brine was added, the phases were separated, and the aqueous phase extracted by 3×150 ml portions of ether. The combined ether phases were washed extensively with water, dried and evaporated. The product was isolated as the hydrochloride by precipitation from acetone/ether. Compound (102) yield 31 g. M.p. 135°–137° C.

The following compounds were prepared essentially in the same manner.

(+−) trans
4-(3-bromophenyl)-3-(4-trifluoromethylphenoxymethyl)-1-butylpiperidine, HCl (103)

From 59 mmol of compound (97), reaction time 40 minutes, triturated from ether. Compound (103) yield 26.3 g. M.p. 111°–113° C.

(+−) trans
4-(2-bromophenyl)-3-(4-trifluoromethylphenoxymethyl)-1-pentylpiperidine, HCl (104)

From 20.6 mmol of compound (98), reaction time 60 min. Triturated from ether. Compound (104) yield 7.5 g. M.p. 147.5°–148.5° C.

(+−) trans
4-(2-trifluoromethylphenyl)-3-(4-trifluoromethylphenoxymethyl)-1-pentylpiperidine, HCl (105)

From 15 mmol of compound (99), reaction time 40 min., crystallization unsuccessful. Obtained as a hard glass by evaporation from EtOAc at 120° C., 0.5 torr. Compound (105) yield 2.2 g. M.p. 135°–138° C.

EXAMPLE 20

(+−) trans
4-(4-cyanophenyl)-3-(4-trifluoromethylphenoxymethyl)-1-pentylpiperidine, HCl (107)

19.2 mmol of compound (102) in 100 ml methylene chloride was washed with 2×20 ml 2N NaOH, 20 ml brine, evaporated, and reevaporated from 50 ml DMF. The product was dissolved in 20 ml DMF, 40 mmol of CuCN(I) was added and the suspension was refluxed for 8 h., protected from moisture by a $CaCl_2$-guard tube. The resulting mixture was dissolved in 80 ml 30% vol/vol ethylenediamine plus 100 ml ether, with stirring during one hour. The phases were separated, and the ether phase was extracted by 2×40 ml 10% NaCN-solution, 2×40 ml water, dried and evaporated. Column chromatography on silica with EtOAc yielded 5.3 g of the product as a brown oil. 3.1 g of this material was precipitated as the hydrochloride from acetone/ether. Compound (107) yield 2.88 g. M.p. 110°–115° C.

(+−) trans
4-(4-carboxyphenyl)-3-(4-trifluoromethylphenoxymethyl)-1-pentylpiperidine, HCl (108)

5.1 mmol of compound (107) was hydrolyzed by refluxing, in a mixture of 25 ml EtOH and 15 ml 2N NaOH, for 12 hours. The ethanol was evaporated, the solution neutralized by addition of dilute HCl, brine was added and the product extracted into methylene chloride, washed with water and evaporated. The product was crystallized as the hydrochloride by slow evaporation from acetone. Compound (108) yield 1.4 g. M.p. 250° C. d.

(+−) trans
4-(4-carbamoylphenyl)-3-(4-trifluoromethylphenoxymethyl)-1-pentylpiperidine, HCl (109)

1.9 mmol of compound (107) was suspended in 10 ml 2N NaOH, 10% $H_2O_2$, refluxed for 3 hours, and left at room temperature for 3 days. The solution was acidified (to avoid foaming) and evaporated, partitioned between 2N NaOH and ether, and the ether phase washed with water, dried and evaporated to a yellow powder which was recrystallized from 1:1 EtOAc/heptane. Compound (109) yield 170 mg. M.p. 167.5°–168.5° C.

EXAMPLE 21

(+−) trans
4-(4-ethylcarbamoylphenyl)-3-(4-trifluoromethylphenoxymethyl)-1-pentylpiperidine, HCl (110)

2 mmol of compound (108) was refluxed in a mixture of 5 ml chloroform and 3.7 ml thionyl chloride for 80 min., evaporated, and re-evaporated 3 times from chloroform, dissolved in 10 ml dry methylene chloride, and cooled in an ice/water bath. A solution of 50 mmol of ethylamine in 10 ml 4N NaOH was added with vigorous stirring, and the mixture stirred for 1 hour at room temperature. The chloroform phase was separated, washed with base, water, dried and evaporated. The product was then isolated by precipitation of the hydrochloride from acetone/ether. Compound (110) yield 760 mg. M.p. 211°–214° C.

(+−) trans
4-(4-phenethylcarbamoylphenyl)-3-(4-trifluoromethylphenoxymethyl)-1-pentylpiperidine, HCl (111)

1 mmol of compound (108) was refluxed in a mixture of 5 ml chloroform and 2 ml thionyl chloride for 80 minutes, evaporated, and re-evaporated 3 times from methylene chloride and dissolved in 10 ml dry methylene chloride. 2.5 mmol of phenethyl amine was dropwise added with stirring, and the solution stirred for 30 min. The methylene chloride solution was then washed with water, dried, and evaporated to give a mass which was precipitated from acetone/ether. Compound (111) yield 400 mg. M.p. 192°–195° C.

(+−) trans
4-(4-(N-(2-hydroxy-2-phenylethyl)carbamoyl)phenyl)-3-(4-trifluoromethylphenoxymethyl)-1-pentylpiperidine, HCl (112)

1 mmol of compound (108) was refluxed in a mixture of 5 ml chloroform and 2 ml thionyl chloride, and dissolved in 10 ml dry methylene chloride. 2.5 mmol of 2-hydroxy-2-phenyl-ethyl amine was dropwise added with stirring, and the solution stirred for 30 minutes. The methylene chloride solution was then washed with water, dried and evaporated, to give a mass which was precipitated from acetone/ether. Compound (112). Yield 350 mg. M.p. 179°–181° C.

EXAMPLE 22

(+−) trans
4-(4-hydroxymethylphenyl)-3-(4-trifluoromethylphenoxymethyl)-1-pentylpiperidine, oxalate (113)

To a suspension of 1.23 mmol of LiAlH$_4$ in 10 ml diglyme, was dropwise added a suspension of compound (108) with stirring at 0° C., and the stirring continued for one hour. Another 1.23 mmol portion of LiAlH$_4$ was added, and the stirring continued for 2 h at room temperature. Excess hydride was destroyed by addition of water, allowing the temperature to rise to 50° C., and the solution filtrated. The precipitate was extracted by ether, and the combined filtrate and extracts evaporated. The product was isolated by column chromatography on silica with MeOH/methylene chloride 1:9, and the oxalate salt isolated as a hard glass. Compound (113) yield 290 mg. M.p. 68°–70° C.

(+−) trans
4-(4-aminomethylphenyl)-3-(4-trifluoromethylphenoxymethyl)-1-pentylpiperidine, HCl (114)

3.2 mmol of compound (107) was partitioned between 10 ml methylene chloride and 10 ml 2N NaOH, 10 ml of toluene was added to the methylene chloride phase and evaporated, and the product re-evaporated from 25 ml toluene and dissolved in 10 ml dry ether. This solution was dropwise added to a suspension of 3.2 mmol of LiAlH$_4$ in 10 ml ether, the mixture refluxed for 10 minutes, and further stirred for 30 min. at room temperature. 10 ml of 4N NaOH solution was added, the ether phase separated, and the aqueous phase extracted with 2×10 ml ether. The combined gelly ether solutions was dried with MgSO$_4$, extracted with stirring, filtered through a column of MgSO$_4$, and the MgSO$_4$ was extracted with ether. The combined extracts and filtrate were evaporated, and the hydrochloride isolated by evaporation from acetone. The compound was then dissolved in water, washed with EtOAc, basified and extracted into ether, dried and evaporated. The product was then isolated as the hydrochloride by evaporation from acetone as a hard glass. Compound (114) yield 1.2 g. M.p. 140°–160° C.

EXAMPLE 23

(+−) trans
4-(5-N-methylindolinyl)-3-hydroxymethyl-1-pentylpiperidine (115)

186 mmol of N-methylindolin-5-carbaldehyde in 300 ml EtOAc was slowly added over 30 minutes to a suspension of 465 mmol sodium ethylate in 300 ml EtOAc with stirring, maintaining the temperature below 10° C. Stirring was continued for one hour while the temperature was allowed to increase to room temperature. A solution of 204 mmol of ethyl N-pentylamidomalonate in 100 ml EtOAc was slowly added, and the stirring continued overnight. 123 ml of 25% acetic acid water was added, and the organic phase washed with brine and evaporated. The residue was dissolved in 300 ml toluene, dried with K$_2$CO$_3$ with stirring for one hour, filtered and evaporated to give 60 g of oil, which was dissolved in 100 ml THF.

This solution was slowly added to a stirred suspension of 271 mmol of LiAlH$_4$ in 200 ml THF plus 150 ml toluene, maintaining the temperature below 10° C. Stirring was continued at room temperature overnight. Residual hydride was destroyed by addition of water, followed by 500 ml 6N HCl, maintaining the temperature below 20° C. with an ice/water bath. The phases were separated, and the aqueous phase extracted with 8×300 ml methylene chloride. 120 g solid NaOH was slowly added to the aqueous phase, and the precipitate filtered through hyflo. The precipitate was twice extracted with ether, combined with the flitrate, and washed with water, dried, and evaporated to give an oil, which was triturated by 50 ml EtOAc overnight. The precipitate was filtered, and washed extensively with icecold EtOAc until almost colorless. Compound (115) yield 8.3 g. M.p. 97°–99.5° C.

(+−) trans
4-(5-N-methylindolinyl)-3-(4-trifluoromethylphenoxymethyl)-1-pentylpiperidine, HCl (116)

This compound was prepared as in example 19, from 15.8 mmol of compound (115). Reaction time 45 min. Compound (116) yield 8 g. M.p. 70°–75° C. d.

We claim:
1. A compound of formula I

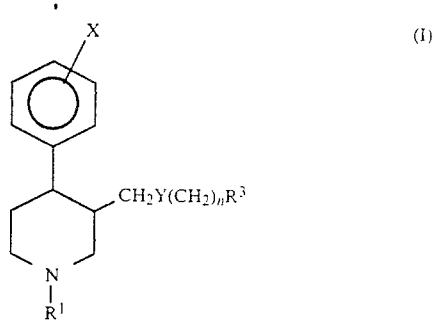

wherein
R$^3$ is 3,4-methylenedioxyphenyl, phenyl or naphthyl, each of which may be optionally substituted with halogen, amino, amino which is substituted with one or two C$_{1-6}$-alkyl groups, C$_{1-6}$-alkoxy, cyano, trifluoromethyl, C$_{2-6}$-alkenyl, C$_{1-6}$-alkyl, C$_{3-5}$-alkylene, trifluoromethoxy, hydroxy or C$_{1-4}$-alkyl substituted with hydroxy;

n is 0, 1, 2, 3 or 4;

R$^1$ is hydrogen, straight or branched C$_{1-8}$-alkyl, C$_{1-8}$-alkoxy-C$_{1-8}$-alkyl, C$_{3-8}$-cycloalkyl, C$_{2-6}$-alkenyl, C$_{4-8}$-cycloalkylalkyl, acetyl or C$_{2-6}$-alkynyl; and Y is NR wherein R is hydrogen or C$_{1-5}$-alkyl;

X is halogen, C$_{1-6}$-alkyl, C$_{2-6}$-alkenyl, C$_{3-8}$-cycloalkyl, C$_{4-8}$-cycloalkylalkyl, C$_{1-6}$-alkoxy, cyano, mono- or poly- halogenated C$_{1-6}$-alkyl, hydroxy or hydrogen; or a pharmaceutically acceptable salt thereof.

2. The compound according to claim 1, wherein n is 0.

3. The compound according to claim 1, wherein n is 1.

4. The compound according to claim 1, wherein $R^1$ is butyl.

5. The compound according to claim 1, wherein X is hydrogen.

6. A compound according to claim 1 which is:

1-butyl-3-(4-methoxybenzylaminomethyl)-4-phenyl-piperidine;

1-butyl-3-(4-trifluoromethylphenylaminomethyl)-4-phenylpiperidine;

(−) trans-1-butyl-3-(2-phenylethylaminomethyl)-4-phenylpiperidine; or a pharmaceutically acceptable salt thereof.

7. A pharmaceutical composition for treating anoxia, cerebral ischemia, migraine or epilepsy comprising an effective amount of a compound according to claim 1 together with a pharmaceutically acceptable carrier or diluent.

8. The pharmaceutical composition according to claim 7 in the form of an oral dosage unit containing 1–100 mg of the active compound.

9. A method of treating anoxia, cerebral ischemia, migraine or epilepsy, comprising administering to a subject in need thereof an effective amount of a compound according to claim 1.

10. A method of treating anoxia, cerebral ischemia, migraine or epilepsy, comprising administering to a subject in need thereof a pharmaceutical composition according to claim 7.

* * * * *